United States Patent [19]

Hadamik et al.

[11] Patent Number: 5,055,231

[45] Date of Patent: Oct. 8, 1991

[54] REACTION PRODUCTS OF BORIC ACID AND ALKANOLETHERAMINES AND THEIR USE AS CORROSION INHIBITORS

[75] Inventors: Franz-Josef Hadamik, Bad Soden; Wilfried Kappa, Steinau an der Strasse; George F. Urban, Bensheim, all of Fed. Rep. of Germany

[73] Assignee: REWO Chemische Werke GmbH, Fed. Rep. of Germany

[21] Appl. No.: 321,981

[22] Filed: Mar. 10, 1989

[30] Foreign Application Priority Data

Mar. 12, 1988 [DE] Fed. Rep. of Germany ....... 3808372

[51] Int. Cl.$^5$ .......................... C23F 11/10; C07F 5/02
[52] U.S. Cl. .................................. 252/391; 252/392; 252/49.6; 252/389.41; 564/8; 564/9
[58] Field of Search ................... 252/389.41 AB, 49.6, 252/49.9, 391, 392; 564/8, 9

[56] References Cited

U.S. PATENT DOCUMENTS

| | | | |
|---|---|---|---|
| 2,866,811 | 12/1958 | Irish | 252/49.6 |
| 2,994,713 | 8/1961 | Lane | 252/49.6 |
| 2,999,064 | 9/1961 | Sluhan | |
| 3,186,946 | 6/1965 | Sluhan | 252/49.6 |
| 3,200,074 | 8/1965 | Knowles | 252/49.6 |
| 3,227,739 | 1/1966 | Versteeg | 252/389.41 |
| 3,316,287 | 4/1967 | Nunn et al. | 252/49.6 |
| 3,518,193 | 6/1970 | Cyba | 252/49.6 |
| 3,642,652 | 2/1972 | Birgy | 252/389.41 |
| 3,969,236 | 7/1976 | Waldstein | 252/49.6 |
| 4,022,713 | 5/1977 | Waldstein | |
| 4,297,236 | 10/1981 | Dieryl et al. | 252/389.41 |
| 4,522,632 | 6/1985 | Horodysky et al. | 252/49.6 |
| 4,537,692 | 8/1985 | Horodysky et al. | 252/49.6 |
| 4,652,387 | 3/1987 | Andress Jr. et al. | 252/49.6 |
| 4,743,386 | 5/1988 | Doner et al. | 252/389.41 |
| 4,780,227 | 10/1988 | Doner et al. | 252/49.6 |

FOREIGN PATENT DOCUMENTS

| | | |
|---|---|---|
| 1143953 | 7/1965 | Fed. Rep. of Germany . |
| 2007229 | 3/1969 | Fed. Rep. of Germany . |
| 1298672 | 3/1970 | Fed. Rep. of Germany . |
| 1620447 | 4/1970 | Fed. Rep. of Germany . |

OTHER PUBLICATIONS

Corrosion Inhibiting Piperazine Derivatives Contg. Boron-Useful in Coolants, Lubricants, Cutting Fluids etc., AN 75-55760w/34, PN DE 1620447-B.
Corrosion Inhibitors Comprising One or Several Alkanolamine Borates, AN No. #70-59426R/33, PN DE 2007229-A.
Lubricating Concentrate, Patent Number 1143953, German 2-21-63, vol. 3, No. 12, "Metallurgy".
Corrosion-Inhibiting, Patent Number 1,298,672, German 7-3-69, vol. 9, No. 32, "Metallurgy".

Primary Examiner—Deborah L. Kyle
Assistant Examiner—Valerie Fee
Attorney, Agent, or Firm—Scully, Scott, Murphy & Presser

[57] ABSTRACT

This invention is directed to a product formed by reacting under condensation conditions, in effective molar ratios, an orthoboric acid and an alkanoletheramine having the formula

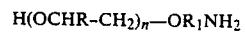

$$H(OCHR-CH_2)_n-OR_1NH_2$$

wherein
R is hydrogen or lower alkyl, $R_1$ is lower alkylene and n is 1-5.

17 Claims, No Drawings

REACTION PRODUCTS OF BORIC ACID AND ALKANOLETHERAMINES AND THEIR USE AS CORROSION INHIBITORS

This invention relates to a product formed from the reaction of boric acid and alkanoletheramines and its use as a corrosion inhibitor.

BACKGROUND OF THE INVENTION

In the last few years, the metal working industry has set high standards concerning the quality of cooling lubricants that is used therein.

In addition to good cooling and lubricating properties, these lubricants must provide excellent protection against corrosion, stability against microorganisms, and in those instances where skin contact is unavoidable, the compositions should be nontoxic and dermatologically safe.

In other technical areas of application, where water or aqueous solutions are used in the presence of corrosion susceptible metals or their alloys, there is a constant need for adequate corrosion protection.

In the past, numerous corrosion inhibitors were prepared which have proven to be effective. These include salts or condensation products of mono-, di- or trialkanolamines and boric acid in conjunction with organic acids if needed.

Mixtures of boric acid, unsaturated fatty acids and alkanolamines are known from U.S. Pat. No. 2,999,064. These aqueous solutions are used as cutting fluids and show the best microbiocidal properties. However, there are many disadvantages associated therewith. For example, besides the disadvantage of foaming, the anti-corrosive character of these mixtures is inadequate.

In DE-OS 1620447 and DE-OS 2007229, salts or condensation products of alkanolamines and orthoboric acid are described as foamless water-hardening nonreactive rust inhibitors with fungistatic and bacteriostatic action. The corrosion inhibiting action of these compositions has proven to be inadequate in practice.

When secondary amines are used, however, it is impossible to exclude formation of nitrosamine because of their reaction with other components in the final aqueous formulation or under conditions of use. Moreover, the toxicity of nitrosamines are well known.

Nitrosamine formation does not occur if primary amines are used. Hence, as described in U.S. Pat. No. 4,022,713, the reaction product of monoalkanolamines having 1 to 3 carbon atoms in the alkanol chain is not problematic in this regard. When used as a rust inhibitor, however, this product does not meet the demands of practical applications. Additionally, when used as cutting oils or as a cooling lubricant, the adhesiveness of its surface-dried residues has always been troublesome.

SUMMARY OF THE INVENTION

The compounds of the present invention overcome the inadequacies of the prior art. The present invention is directed to compounds which are water soluble; which can be used in aqueous solutions and, if necessary, in co-usage with other components; have excellent corrosion inhibiting action, do not produce foam; exhibit microbiocidal and microbiostatic action at the working concentrations; and do not form adhesive surface-dried residues. In addition, the compounds of the present invention do not form any nitrosoamines during storage or under conditions of use.

In accordance therewith, the present invention is directed to a product formed under condensation condition by reacting, in effective molar ratios, orthoboric acid or analogs thereof (hereinafter orthoboric acid and its analogs will be designated as orthoboric acid) and alkanoletheramines of the general formula:

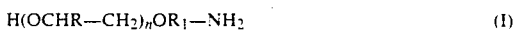

$$H(OCHR-CH_2)_n OR_1 - NH_2 \qquad (I)$$

wherein R is hydrogen or lower alkyl; $R_1$ is lower alkylene and
n is 1-5.

A preferred embodiment of the present invention is a structure of Formula I:

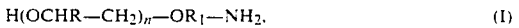

$$H(OCHR-CH_2)_n - OR_1 - NH_2. \qquad (I)$$

wherein R is hydrogen or methyl; $R_1$ is $-(CH_2)_2-$, $-(CH_2)_3-$ or

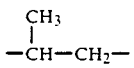

$$-\underset{\underset{CH_3}{|}}{CH}-CH_2-$$

and
n is 1-5

The present invention is also directed to a corrosion inhibitor which may be containing an anti-corrosive effective amount of the product of Formula I described hereinabove.

DETAILED DESCRIPTION OF THE INVENTION

The new products of the present invention meet all the requirements of the industry with respect to actions against microorganisms, corrosion inhibiting action, foam content, toxicity and dermatological characteristics. Furthermore, the products of the present invention are surprisingly found to possess excellent viscosity characteristics and are extremely easy with which to work. Another advantage of the reaction products of the present invention is that the surface dried residues are non-adhesive.

As described hereinabove, the present invention is directed to the products formed by reacting orthoboric acid and alkanqletheramines of the formula

$$H(OCHRCH_2)_n - OR_1 - NH_2 \qquad I$$

wherein R is lower alkyl or hydrogen $R_1$ is lower alkylene and n is 1-5.

As used herein, the term lower alkyl, when used alone or in combination with other groups, is an alkyl chain containing 1 to 6 carbon atoms. Said term includes the straight-chain alkyl groups as well as the branched group. It includes such groups as methyl, ethyl, propyl, isopropyl, butyl, isobutyl, t-butyl, sec-butyl, pentyl, amyl, neopentyl, hexyl and the like. The preferred alkyl group contains 1-3 carbon atoms.

The term lower alkylene refers to an alkylene chain containing 1 to 6 carbon atoms. Said term includes the straight chains as well as the branched alkylene chains. It includes such groups as $-CH_2-$, $-CH_2-CH_2-$, $-CH(CH_3)CH_2-$,

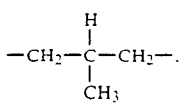

and the like. The preferred alkylene chain contains 1-3 carbon atoms.

It is preferred that R is hydrogen or methyl. The especially preferred value of R is hydrogen.

$R_1$ is preferably $-(CH_2)_2-$, $-(CH_2)_3-$ or

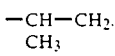

It is especially preferred that $R_1$ is $-(CH_2)_2-$.

The preferred values of n are 1 and 2. It is especially preferred that n is 1.

The preferred alkanoletheramine used in the present invention have the structure indicated in Formula I wherein R is hydrogen or methyl, $R_1$ is $-(CH_2)_2-$, $-(CH_2)_3-$ or $-CH(CH_3)-CH_2-$ and n is 1-5.

Especially preferred alkanoletheramines are those in which R is hydrogen, $R_1$ is $-(CH_2)_2-$ and n is 1 or 2.

An even more preferred alkanoletheramine is one in which R is hydrogen, $R_1$ is $-(CH_2)_2-$ and n is 1.

The products of the present invention are produced by condensation of ortho-boric acid and the alkanoletheramine of general Formula I in effective molar ratios of boric acid: alkanoletheramine. It is preferred that said ratio ranges from about 1:1 to about 1:6. The most preferred molar ratio ranges from about 1:1 to about 1:3. It is especially preferred that the molar ratio is greater than 1:3 but less than or equal to 1:1.

As indicated hereinabove, these products are useful as a corrosion inhibitor. However, products formed by the reaction of effective amounts of orthoboric acid and dialkanoletheramine or trialkanoletheramines of Formula II are also effective. These compounds have the formula $$[H(OCHRCH_2)_n-OR_1]_m NR'_z \qquad II$$

wherein R and $R_1$ and n have the aforesaid meanings, m is 2, or 3, z is 3 minus m and R' is a chemical bond, hydrogen or lower alkyl group containing 1 to; 6 carbons but preferably 1-3 carbon atoms, e.g. methyl, ethyl or isopropyl.

When the compound of Formula II is a dialkanoletheramine, m is 2 and z is 1. On the other hand, when the compound of Formula II is a trialkanoletheramihe, m is 3 and z is 0, and therefore R' is a chemical bond and is not present.

The products formed from orthoboric acid and dialkanoletheramines or trialkanoletheramines are also contemplated by the present invention. It is preferred that the effective molar ratios of orthoboric acid and the compounds of Formula II range from about 1:1 to about 1:6. The preferred molar ratio ranges from about 1:1 to about 1:3. It is especially preferred that the molar ratio is greater than 1:3 but less than or equal to 1:1.

The monoalkanoletheramines are preferred for toxicological and dermatological reasons. However, in those situations in which human contact is not contemplated and where nitrosamine build-up cannot take place, the products of the reaction between orthoboric acid and compounds of Formula II can be used.

Alkanoletheramine of general Formula I and II are commercially available as commercial mixtures containing low concentrations of impurities, e.g., homologs, and can be used as a reactant without further purification. However, by purification techniques known to one skilled in the art, such as distillation, the homologs can be removed to any desired degree.

The reaction of the orthoboric acid and the alkanoletheramine can be run in the absence or presence of an inert solvent.

In the reaction, the alkanoletheramine is heated to about 70°-80° C. and the orthoboric acid is slowly added with stirring. The reaction mixture is then further heated. The reaction usually takes place at effective condensation temperatures ranging from about 70° C. to about 160° C., although it is preferred that the reaction be run at 80° C. The reaction is normally completed within 2-3 hours.

During the reaction water is released. The amount of water released, which will vary according to the reaction temperature and time, is removed from the reaction mixture under atmospheric pressure.

The reaction products of the present invention can be employed as concentrates ranging from 1 to 50% by weight of the total concentrate. They can also be used in applications involving aqueous solutions or emulsion at about 0.1 to 6% by weight, and preferably 0.2-3% by weight of the total mixture.

The concentrates and aqueous solutions can additionally contain any of the other usual corrosion inhibitors, for example, aryl- or alkyl-sulfonamidocarboxylic acids having the general Formula III,

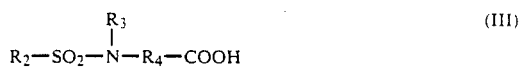

wherein $R_2$ is an alkyl chain having 12 to 22 carbon atoms or an aryl group having 6 to 10 carbon atoms; $R_3$ is a hydrogen, methyl, ethyl, hydroxymethyl, cyanoethyl or carboxymethyl group and $R_4$ is an alkylene group having 1 to 6 carbon atoms. The term alkyl as used herein is a hydrocarbon chain which may be straight chain or branched. The lower alkyl groups, as used herein, contain 1 to 6 carbon atoms and may include methyl, ethyl, propyl, isopropyl, butyl, isobutyl, t-butyl, sec-butyl, pentyl, hexyl, isopentyl, isohexyl, neopentyl, and the like.

An aryl group is an aromatic ring containing 6 to 10 ring carbon atoms and up to a total of 14 carbon atoms. It includes phenyl, α-naphthyl and β-naphthyl.

The compounds of Formula III are described in DE-PSen 900,041; 1,298,672 and 1,143,953 and can be used in amounts ranging from 2 to 50% by weight relative to the total mixture of the reaction product and the sulfonamidocarboxylic acid. The preferred sulfonamido carboxylic acids are the arylsulfonamidocarboxylic acids like -e(benzylsulfonyl-N-methylamino)-n-caproic acid or -e(toluoylsulfonyl-N-methylamino)-n-caproic acid.

If need be, other of the usual substances that are known in the art can also be added, such as spindle oils, emulsifiers fatty acids, polyhydric alcohols and chelating agents.

These water soluble corrosion inhibitors of the present invention form clear solutions and transparent emulsions, and are practically foam-free. These corrosion inhibitors can be used as coolants, lubricants and cleaning agents in the metal working industry as well as in commercial pressurization and cooling processes.

The following examples further illustrate the present invention.

EXAMPLES

A) Manufacturing Instructions:

Production of the Reaction Products of the Present Invention

EXAMPLE 1

315 g diglycolamine (3 moles) was heated to 70° C. and 62 g ortho-boric acid (1 mole) was then added with stirring and heated to 80° C. until a clear solution resulted. The yield is about 360 g of a clear water soluble liquid having low viscosity that can be used as a corrosion inhibitor.

EXAMPLE 2

315 g diglycolamine (3 moles) was heated to 70° C. and 62 g ortho-boric acid (1 mole) was then added with stirring and heated to 150° to 160° C. After a reaction time of 3 hours, 9 ml of water (0.5 moles) was distilled away. The yield was about 350 g of a clear liquid having medium viscosity.

EXAMPLE 3

210 g diglycolamine (2 moles) was heated to 70° C. and 62 g ortho-boric acid (1 mole) was slowly added thereto and reacted at 80° C. for 1 to 2 hours. The yield was about 250 g of a clear liquid having medium viscosity.

EXAMPLE 4

210 g diglycolamine (2 moles) was heated to 70° C. and 124 g ortho-boric acid (2 moles) was slowly stirred into the mixture and reacted at 80° to 85° C. until a clear solution resulted. The yield after 2 to 3 hours was a clear liquid having medium viscosity.

EXAMPLE 5

315 g diglycolamine (3 moles) was heated to about 70° C., 186 g ortho-boric acid (3 moles) was slowly added and then the temperature raised slowly to 150° C. After a reaction time of about 3 hours, 46 g (2.5 moles) of water was distilled away. The product was a clear, high viscous liquid.

EXAMPLE 6

A mixture of 90% by weight of the product of Example 4 at 40° to 50° C. was made with 10% by weight of an arylsulfonamidocarboxylic acid (HOSTACOR H, trademark of Hoechst). The result was a clear, low viscous fluid that can be used as a corrosion inhibitor.

EXAMPLE 7

450 g triglycolamine (3 moles) was heated to 80° C. and 62 g ortho-boric acid (1 mole) was slowly added with stirring and reacted for 1½ to 2½ hours until a clear solution having the desired viscosity was obtained.

EXAMPLE 8

360 g aminopropylglycolether (3 moles) was heated to 80° C. and 62 g ortho-boric acid (1 mole) was slowly added with stirring and reacted for 1½ to 2½ hours until a clear solution having the desired viscosity was obtained.

Comparison Product A 62 g ortho-boric acid (1 mole) was heated at 90° C. with 315 g diethanolamine (3 moles) until a clear solution resulted.

Comparison Product B 62 g ortho-boric acid (1 mole) was heated at 90° C. with 62 g monoethanolamine (1 mole). The result was a clear, high viscous liquid.

B) Commercial Testing

Various aqueous solutions of the reaction products from Examples 1 to 8 were examined for inhibition of corrosion in accordance with the rust protection test described in DIN 51,360, Part 2 (Spane filter test). The results are shown in Table 1.

TABLE 1

| Product | Test Result from DIN 51,360, Part 2 % of product present in tested sample | | |
|---|---|---|---|
| | 1.5% | 2% | 2.5% |
| Comparison Product A | 4 | 4 | 3 |
| Comparison Product B | 4 | 2 | 0 |
| Example 1 | 3 | 1 | 0 |
| Example 2 | 3 | 1 | 0 |
| Example 3 | 4 | 2 | 0 |
| Example 4 | 4 | 3 | 0 |
| Example 5 | 4 | 3 | 0 |
| Example 6 | 1 | 0 | 0 |
| Example 7 | 3 | 1 | 0 |
| Example 8 | 3 | 1 | 0 |

Rating Value:
0 = no corrosion
1 = trace corrosion
2 = slight corrosion
3 = moderate corrosion
4 = strong corrosion C) Formulations Examples 1 to 8, prepared as as above, are formulated into water soluble biostable cooling lubricants by adding the ingredients listed in each of the following examples:

EXAMPLE 9

35 g spindle oil[1]
12 g fatty acid diethanolamide[2]
9 g nonionic emulsifier[3]
23 g reaction product from Example 1
14 g water
3 g additional material[4/1]
4 g additional material[4/2]

EXAMPLE 10

32 g spindle oil[1]
14 g fatty acid diethanolamide[2]
9.5 g nonionic emulsifier[3]
22 g reaction product from Example 4
14 g water
5.5 g oleic acid
3 g additional material[4/2]

EXAMPLE 11

40 g spindle oil
15 g fatty acid diethanolamide[2]
8 g nonionic emulsifier[3]
22 g reaction product of Example 3
9 g water
3 g additional material[4/1]
3 g additional material[4/2]

EXAMPLE 12

35 spindle oil[1]
12 g fatty acid diethanolamide[2]
9 g nonionic emulsifier[3]
23 g reaction product from Example 6
14 g water
3 g additional material[4/1]
4 g additional material[4/2]

EXAMPLE 13

32 g spindle oil[1]
14 g fatty acid diethanolamide[2]
9.5 g nonionic emulsifier[3]
22 g reaction product from Example 1
14 g water 5.5 g oleic acid 3 g additional material[4/2]

EXAMPLE 14

35 g spindle oil[1]
12 g fatty acid diethanolamide[2]
9 g nonionic emulsifier[3]
23 g reaction product from Example 7
14 g water
3 g additional material[4/1]
4 g additional material[4/2]

EXAMPLE 15

35 g spindle oil[1]
12 g fatty acid diethanolamide[2]
9 g nonionic emulsifier[3]
23 g reaction product from Example 8
14 g water
3 g additional material[4/1]
4 g additional material[4/2]

COMPARISON EXAMPLE 16

35 g spindle oil[1]
12 g fatty acid diethanolamide[2]
5 g nonionic emulsifier[3]
29 g comparison product A
14 g water
3 g additional material[4/2]
2 g additional material[4/1]

COMPARISON EXAMPLE 17

30 g spindle oil[1]
12 g fatty acid diethanolamide[2]
7 g nonionic emulsifier[3]
20 g comparison product B
8 g diethanolamine
14 g water
3 g oleic acid[4/2]
6 g oleic acid
3 g additional material[4/2]

Explanations

[1] Spindle oil made from refined mineral oil having a viscosity at 20° C. of 10 centistokes (cSt).
[2] Fatty acid diethanolamide made from monomeric fatty acids having 8 to 22 carbon atoms.
[3] Fatty alcohols with a chain length of 12 to 18 carbon atoms and having 4 to 6 moles of ethyleneoxide.
[4/1] Fatty acids having a chain length of 12 to 18 carbon atoms.
[4/2] Glycols (preferably diethyleneglycol-monobutylether).

The above concentrates, from Examples 9 to 17, were formulated into 1.5% to 5% aqueous emulsions and were tested in accordance with the procedure described in DIN 51,360 Part 2, as discussed hereinabove. The

TABLE 2

| | | Commercial Testing | | |
| --- | --- | --- | --- | --- |
| Example | Reaction Product | Concentration of Aqueous Test by DIN 51,360, Part 2 | | |
| | | 1.5% | 2% | 2.5% |
| 9 | Ex. 1 | 3 | 1 | 0 |
| 10 | Ex. 4 | 3 | 0 | 0 |
| 11 | Ex. 3 | 3 | 1 | 0 |
| 12 | Ex. 6 | 2 | 0 | 0 |
| 13 | Ex. 1 | 2 | 0 | 0 |
| 14 | Ex. 7 | 3 | 1 | 0 |
| 15 | Ex. 8 | 3 | 1 | 0 |
| Comparative Examples | | | | |
| 16 | | 4 | 1 | 0 |
| 17 | | 2 | 1 | 0 |

Rating values as described in Table 1.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A product formed by reacting under condensation conditions, orthoboric acid and an alkanoletherammine in the molar ratios of from about 1:1 to about 1:6, said alkanoletheramine having the formula:

$$H(OCHR-CH_2)_n-OR_1NH_2$$

wherein
R is hydrogen or lower alkyl, $R_1$ is lower alkylene and
n is 1-5.

2. The product of claim 1 in which the lower alkyl and alkylene group contain 1-3 atoms.
3. The product of claim 1 wherein R is hydrogen.
4. The product of claim 1 where $R_1$ is $-(CH_2)_2-$.
5. The product of claim 1 in which the molar ratio is from about 1:1 to about 1:3.
6. A corrosion inhibitor comprising an anti-corrosive effective amount of the product according to claim 1.
7. A product formed by reacting under condensation conditions, orthoboric acid and an alkanoletherammine in which the molar ratios are from about 1:1 to about 1:6, said alkanoletheramine having the formula:

$$H(OCHR-CH_2)_nOR_1-NH_2.$$

wherein
R is hydrogen or methyl;
$R_1$ is $-(CH_2)_2-$, $-(CH_2)_3-$ or $$-CH-CH_2-$$
$$\phantom{-}|$$
$$\phantom{-}CH_3$$

and
n is 1 to 5.

8. The product of claim 5 where R is hydrogen, $R_1$ is $-(CH_2)_2-$ and n is 1 or 2.
9. The product of claim 7 wherein the molar ratio of orthoboric acid to alkanoletheramine is from about 1:1 to about 1:3.

10. A corrosion inhibitor comprising an anti-corrosive effective amount f the product according to any one of claims 7, 8 and 10.

11. The corrosion inhibitor of claim 6 wherein the product is in the form of a concentrate and is present in amounts ranging from 0.5 to 50% by weight of the total concentrate.

12. The corrosion inhibitor according to claim 6 wherein the product is present in an aqueous solution in amounts ranging from 0.1 to 6% by weight of the total solution.

13. The corrosion inhibitor according to claim 6, wherein a sulfonamide carboxylic acid is additionally present, said sulfonamide carboxylic acid having the formula:

$$R_1-SO_2-\underset{\underset{R_2}{|}}{N}-R_3-COOH$$

wherein $R_1$ is an alkyl group containing 12 to 22 carbon atoms, or an aryl group containing 6 to 10 ring carbon atoms;

$R_2$ is hydrogen, methyl, ethyl, hydroxymethyl, cyanoethyl or carboxymethyl and $R_3$ is an alkylene group containing from 1 to 6 carbon atoms.

14. The corrosion inhibitor according to claim 12 wherein the sulfonamide carboxylic acid is an aryl sulfonamide carboxylic acid.

15. The corrosion inhibitor of claim 13 wherein the aryl sulfonamide carboxylic acid is ε-(benzylsulfonyl-N-methylamino)-n-caproic acid or ε-(toluoylsulfonyl-N-methylamino)-n-caproic acid.

16. The corrosion inhibitor of claim 6 which additionally contains spindle oil, fatty acid diethanolamide, fatty alcohols having a chain length of 12-18 carbon atoms, fatty acids having a chain length of 12-18 carbon atoms or glycols.

17. The product formed by reacting under condensation conditions, orthoboric acid and an alkanoletheramine in which the molar ratios are from about 1:1 to about 1:6, said alkanoletheramine having the formula:

$$[H(OCHR/CH_2)_n-OR_1]_mNR_z$$

wherein R is hydrogen or methyl, $R_1$ is $(CH_2)_2-$, $-(CH_2)_3-$ or $$-\underset{\underset{CH_3}{|}}{CH}-CH_2-$$

n is 1-5
m is 2 or 3
z is 3 minus m 0 and
$R^1$ is hydrogen, or alkyl groups containing 1 to 3 carbon atoms.

* * * * *

UNITED STATES PATENT AND TRADEMARK OFFICE
CERTIFICATE OF CORRECTION

PATENT NO. : 5,055,231
DATED : October 8, 1991
INVENTOR(S) : Franz-Josef Hadamik It is certified that error appears in the above-identified patent and that said Letters Patent is hereby corrected as shown below:

Column 2, line 49: "alkanqletheramines" should read as --alkanoletheramines--

Column 3, line 49: "to;" should read as --to--

Column 3, line 54: "trialkanoletheramihe" should read as --trialkanoletheramine--

Column 4, lines 60 & 61: "-e" should read as --ε- --

Column 7, line 55: delete "3 g oleic acid$^{4/2}$"

Column 8, line 28, Claim 1: "alkanoletherammine" should read as --alkanoletheramine--

Column 8, line 39, Claim 2: "group" should read as --groups--

UNITED STATES PATENT AND TRADEMARK OFFICE
CERTIFICATE OF CORRECTION

PATENT NO. : 5,055,231

DATED : October 8, 1991

INVENTOR(S) : Franz-Josef Hadamik

It is certified that error appears in the above-identified patent and that said Letters Patent is hereby corrected as shown below:

Column 8, line 39, Claim 2: "1-3 atoms" should read as --1-3 carbon atoms--

Column 8, line 42, Claim 4: "-$(CH_2)_2$-." should read as -- -$(CH_2)_2$-, -$(CH_2)_3$- or -$CH(CH_3)CH_2$-.--

Column 8, line 48, Claim 7: "alkanoletherammine" should read as --alkanoletheramine--

Column 8, line 64, Claim 8: "claim 5" should read as --claim 7--

Column 9, line 3, Claim 10: "f" should read as --of--

UNITED STATES PATENT AND TRADEMARK OFFICE
CERTIFICATE OF CORRECTION

PATENT NO. : 5,055,231
DATED : October 8, 1991
INVENTOR(S) : Franz-Josef Hadamik It is certified that error appears in the above-identified patent and that said Letters Patent is hereby corrected as shown below:

Column 9, line 5, Claim 11: "claim 6" should read as --claim 10--

Column 9, line 9, Claim 12: "claim 6" should read as --claim 10--

Column 9, line 14, Claim 13: "claim 6" should read as --claim 10--

Column 9, line 28, Claim 13: "hydroxymethyl." should read as --hydroxymethyl,--

Column 10, line 1, Claim 14: "claim 12" should read as --claim 13--

Column 10, line 4, Claim 15: "claim 13" should read as --claim 14--

UNITED STATES PATENT AND TRADEMARK OFFICE
CERTIFICATE OF CORRECTION

PATENT NO. : 5,055,231
DATED : October 8, 1991
INVENTOR(S) :

It is certified that error appears in the above-identified patent and that said Letters Patent is hereby corrected as shown below:

Column 10, line 8, Claim 16: "claim 6" should read as --claim 10--

Column 10, line 18, Claim 17:

"$[H(OCHR/CH_2)_n-OR_1]_mNR_z$" should read as

--$[H(OCHRCH_2)_n-OR_1]_mNR'_z$--

Column 10, line 28, Claim 17: "minus m 0" should read as --minus m--

Column 10, line 29, Claim 17: "$R^1$" should read as --R'--

Signed and Sealed this

First Day of March, 1994

*Attest:*

BRUCE LEHMAN

*Attesting Officer*     *Commissioner of Patents and Trademarks*